US00PP09504P

United States Patent [19]

Koppe

[11] Patent Number: Plant 9,504

[45] Date of Patent: Apr. 9, 1996

[54] BEGONIA PLANT NAMED 'AZOTUS'

[75] Inventor: Lubbertus H. Koppe, Ermelo, Netherlands

[73] Assignee: M. Koppe B.V., Ermelo, Netherlands

[21] Appl. No.: 361,320

[22] Filed: Dec. 21, 1994

[51] Int. Cl.[6] ..... A01H 5/00

[52] U.S. Cl. ..... Plt./87.18

[58] Field of Search ..... Plt./87.18

*Primary Examiner*—James R. Feyrer

*Attorney, Agent, or Firm*—Foley & Lardner

[57] ABSTRACT

A Begonia plant named Azotus particularly characterized by its flowering throughout the year, double flowers with multi-rowed flower petals, unique purple-red flower color, and good keeping quality through the winter.

3 Drawing Sheets

The present invention relates to a new and distinctive cultivar of Begonia plant, botanically known as *Begonia hiemalis* Fotch and known by the cultivar name Azotus.

The new cultivar was discovered by L. H. Koppe in October 1988 in Ermelo, The Netherlands, as a seedling from a controlled cross of a proprietary *Begonia tuberosa* selection (T-15950) as the seed parent with an unnamed non-proprietary selection of *Begonia socotrana* as the pollen parent.

The new cultivar was asexually propagated for the first time in May 1989 in Ermelo, The Netherlands. Asexual reproduction by leaf cuttings has reproduced the unique features of the new cultivar through successive propagations.

The following characteristics distinguish the new begonia from both its parents and other begonias commercially known and used in the floriculture industry:

1. The seed parent only flowers during long days whereas Azotus flowers throughout the year.
2. The pollen parent has a small single flower whereas Azotus has a double flower.
3. Flower color of the pollen parent is light pink whereas it is purple-red for Azotus.
4. Azotus is very unique in color and cannot be compared to any variety on the market.
5. Azotus is strongly double-flowering with many rows of flower petals.
6. The keeping quality of Azotus is good.
7. Azotus keeps its flower color very well all through the winter.

The accompanying colored photographs were taken Oct. 15, 1994 in 's-Gravenzande, the Netherlands, and illustrate the overall appearance of this cultivar.

Figure 1:
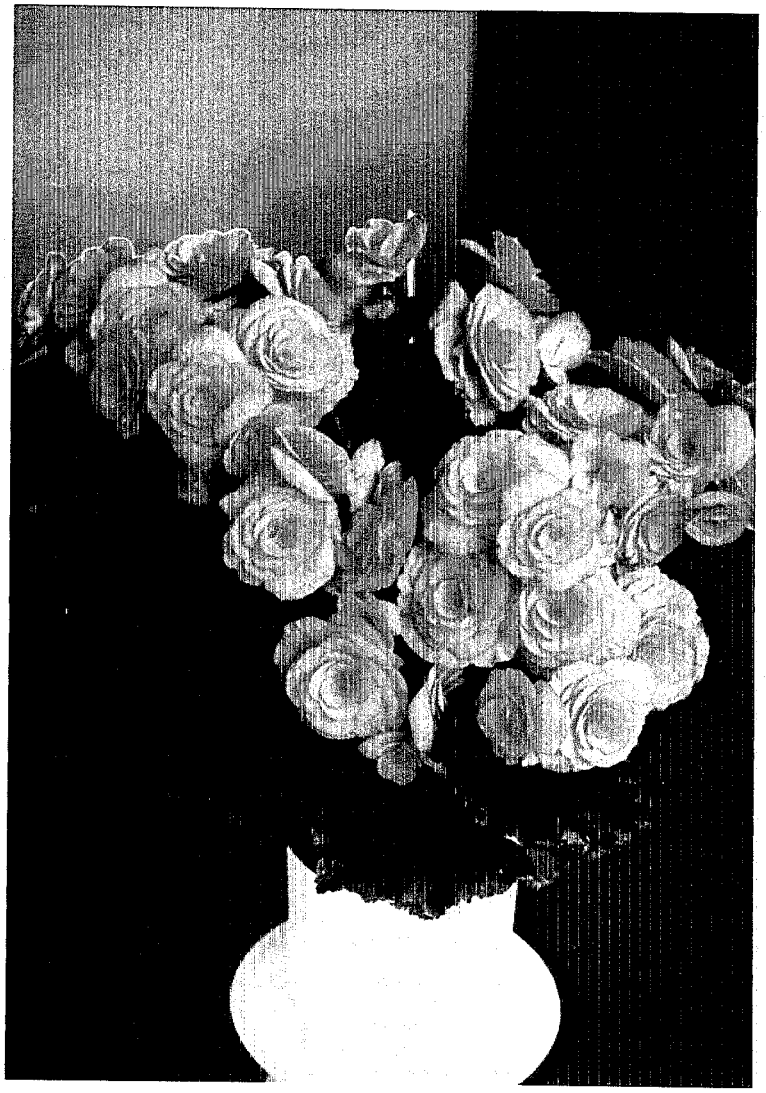
FIG. 1 is an oblique view of the plant grown in a 13 cm plastic pot.
Figure 2:
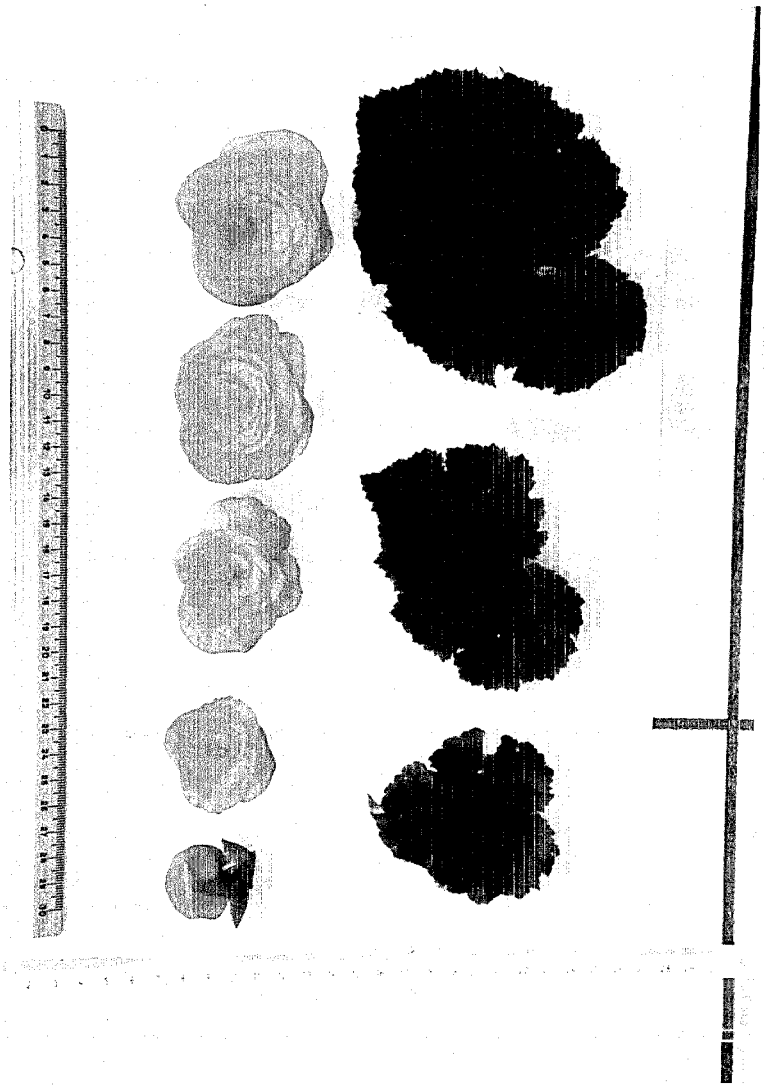
FIG. 2 shows the upperside at the flower and leaves at different development stages.
Figure 3:
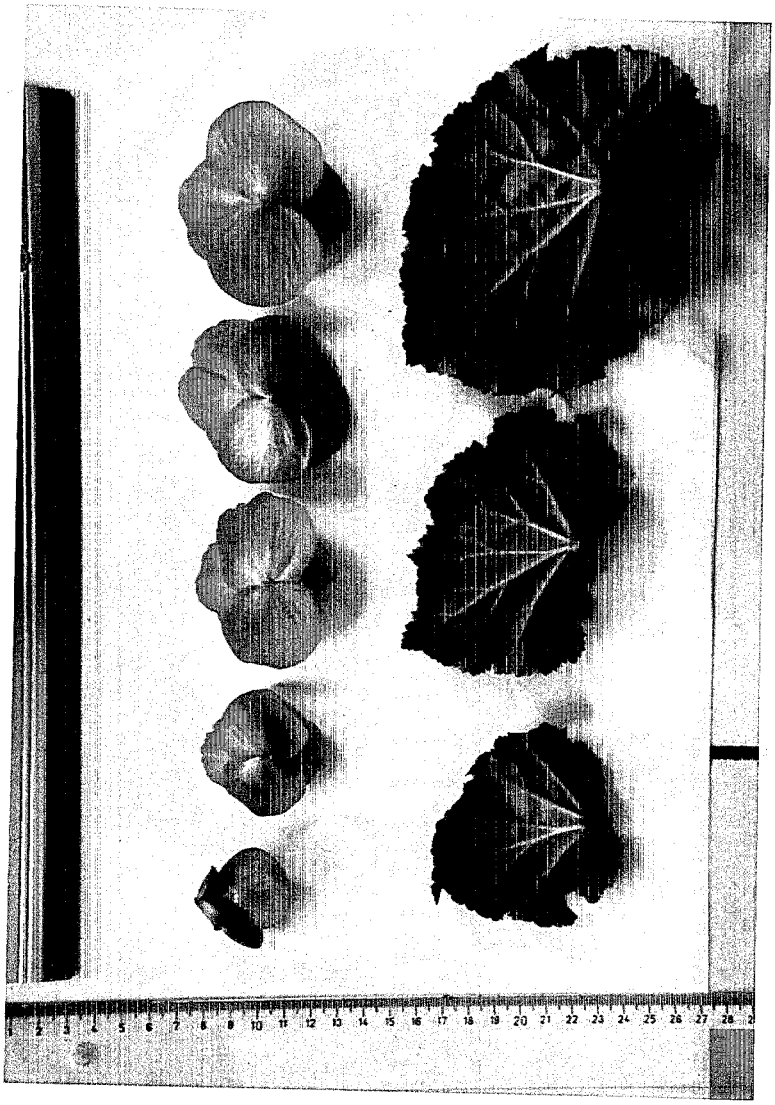
FIG. 3 shows the underside of the flower and leaves at different developmental stages. The colors in these photographs are as true as it is reasonably possible to obtain in a colored reproduction of this type.

The new cultivar is unique and no similar variety exists. The new cultivar Azotus is principally distinguished from other varieties by its unique color. Asexual reproduction of the new cultivar Azotus as performed by applicant at Ermelo, The Netherlands, has demonstrated that the combination of characteristics as herein disclosed for the new cultivar are firmly fixed and retained through successive generations of asexual production. Azotus has not been observed under all possible environmental conditions. The phenotype may vary with variations in environment such as temperature, light intensity and day length, without a change in genotype.

The following is a detailed description of this new Begonia cultivar based on plants produced under commercial practices in Ermelo, The Netherlands. Color references are made to the Royal Horticultural Society (R.H.S.) Colour Chart except where general terms of ordinary dictionary significance are used.

Classification:

*Botanical.*—*Begonia hiemalis* Fotch cv. Azotus.

Parentage:

*Female parent.*—*Begonia tuberosa.*

*Male parent.*—*Begonia socotrana.*

Propagation:

*Type cuttings.*—Terminal and/or leaf cutting.

*Time to root.*—5 weeks at 20°–25° C. summer; 5 weeks at 20°–25° C. winter.

*Rooting habit.*—Spreading. Root system does not form tubers.

*Time for shoot development.*—6–7 weeks after sticking by a top cutting, 7–8 weeks by leaf cutting.

Plant description:

*Form.*—Spreading.

*Habit of growth.*—Upright growth. Height: 31 cm. Width: 29 cm.

*Foliage.*—Medium green. Size: Juvenile leaf: Width 78 mm; length of midrib 65 mm. Half mature: Width 101 mm; length of midrib 75 mm. Mature: Width 122 mm; length of midrib 100 mm. Shape: Unsymmetrical, obliquely cordate; the sinus formed by the basal lobes may be open or closed by overlap of the lobes. The leaves are lightly crimped and crinkled around the periphery. Texture: Glabrous. Margin: Doubly-serrate. Color (young foliage): Top side 135C; under side 148C. Color (mature foliage): Tope side 137A/B; under side 148B/C. Venation: Between 147C and 148C.

Flowering description:

*Flowering habits.*—Floriferous with branched inflorescence.

*Natural flowering season.*—Mid-February until November.

*Flower bud description.*—Sepal is light green turning a little reddish to the tip.

*Flowers borne.*—From axillary buds. The main stalk is about 6 cm. It makes a flower and splits into two other stems. One of these stems makes a flower, and the other splits into two more stems. One of these two stems forms a flower, and the other splits into two stems, etc. The pedicle is about 2 cm and red-green in color. The peduncle is about 6 cm and green to red-green in color.

*Quantity.*—7–9 flowers from one stem out of axillary bud.

*Tepals.*—Shape: Double-flowering. Color (top side in winter when opening): 58B, not fading. Color (underside in winter when opening): 51A Number: Up to 28 petals per flower. Size: Differ by petal and flower. Flower Size: Diameter 70 mm, outer petal 37 mm, inner petal 59 mm.

Reproductive organs: Stamens and pistils are not present.

Disease resistance: Unknown.

Other characteristics: Double-flowering *Begonia hiemalis* Fotch with a unique purple-red color. The double flowers have not reproductive organs and therefore the plant is sterile. While Azotus has a propensity to form branches with or without pinching, pinched plants have a greater propensity to form branches. The internode length is about 3 cm.

I claim:

1. A new and distinct Begonia plant named Azotus, as described and illustrated.

* * * * *